United States Patent
Low et al.

(10) Patent No.: US 8,471,078 B2
(45) Date of Patent: Jun. 25, 2013

(54) PROCESS FOR THE HYDROGENATION OF PENTAFLUOROPROPENE

(75) Inventors: Robert E. Low, Nercwys (GB); Andrew P. Sharratt, Middlewich (GB)

(73) Assignee: Mexichem Amanco Holding S.A. de C.V., Tlalnepantla (MX)

( * ) Notice: Subject to any disclaimer, the term of this patent is extended or adjusted under 35 U.S.C. 154(b) by 0 days.

(21) Appl. No.: 12/735,496

(22) PCT Filed: Jan. 23, 2009

(86) PCT No.: PCT/GB2009/000206
§ 371 (c)(1), (2), (4) Date: Mar. 11, 2011

(87) PCT Pub. No.: WO2009/093047
PCT Pub. Date: Jul. 30, 2009

(65) Prior Publication Data
US 2011/0152586 A1 Jun. 23, 2011

(30) Foreign Application Priority Data
Jan. 23, 2008 (GB) .................................. 0801209.8

(51) Int. Cl.
*C07C 19/08* (2006.01)
(52) U.S. Cl.
USPC ............................ 570/176; 570/123; 570/175
(58) Field of Classification Search
None
See application file for complete search history.

(56) References Cited

U.S. PATENT DOCUMENTS

| | | | |
|---|---|---|---|
| 2,550,953 A | 5/1951 | Barrick | |
| 5,162,594 A | 11/1992 | Krespan | |
| 5,780,695 A | 7/1998 | Kalnes | |
| 6,313,359 B1 * | 11/2001 | Tung et al. | 570/142 |
| 2007/0079324 A1 | 4/2007 | Hallford et al. | |
| 2007/0179324 A1 | 8/2007 | Van Der Puy | |

FOREIGN PATENT DOCUMENTS

| | | |
|---|---|---|
| EP | 0644173 | 3/1995 |
| JP | 769943 | 3/1995 |
| JP | 08169851 | 7/1996 |
| JP | 8510739 | 11/1996 |
| JP | 67281 | 3/1997 |
| JP | 2001/509806 | 7/2001 |
| WO | WO9427940 | 12/1994 |
| WO | WO2008/030440 | 3/2008 |

OTHER PUBLICATIONS

Knunyants et al., Bulletin of the Academy of Sciences of the USSR, Division of Chemical Sciences, 1960, pp. 1312-1317.
International Preliminary Report on Patentability; PCT/GB2009/000206; Aug. 5, 2010.
CN200980102968.2 Office Action dated Aug. 27, 2012.
JP2010543573 Office Action dated Nov. 27, 2012.

* cited by examiner

*Primary Examiner* — Sudhakar Katakam
(74) *Attorney, Agent, or Firm* — Ryan Kromholz & Manion, S.C.

(57) ABSTRACT

A method of providing a blend of tetra- and/or pentafluoro-alkanes comprising hydrogenating a pentafluoropropene.

3 Claims, No Drawings

PROCESS FOR THE HYDROGENATION OF PENTAFLUOROPROPENE

This invention relates to a manufacturing process for converting various unsaturated alkenes to alkanes. In particular, it relates to a method of converting a haloalkene into a desirable haloalkane.

It is desirable that commercially viable routes be found to manufacture tetrafluoropropenes, especially 3,3,3,2-tetrafluoropropene (R-1234yf) and 3,3,3,1-tetrafluoropropene (R-1234ze). In particular, R-1234yf is in demand, as it represents a suitable fluid for use in heat transfer compositions, in particular for use in automobile air conditioning systems. The fluid itself may be used, or it may be used as part of a blend of fluids to provide a suitable heat transfer compositions. R-1234yf has found favour for use in such compositions because of its physical and chemical properties, but also its Global Warming Potential (GWP), which is very low.

A desirable route to the manufacture of suitable tetrafluoropropenes should be cost effective, ideally operating at relatively low temperatures, and/or utilizing mild conditions, and it should ideally be relatively selective.

It is known to produce 1,1,1,2,3,3-hexafluoropropane by hydrogenating hexafluoropropene. In more detail, JP 08-169851 (Daikin Industries Ltd) describes a process for hydrogenating hexafluoropropene with hydrogen in the presence of a palladium catalyst to provide 1,1,1,2,3,3-hexafluoropropane, the process being characterised in that the palladium catalyst is supported on activated carbon. The use of a palladium catalyst supported on carbon in this context is said to provide improvements to the process in terms of prolonging catalyst activity.

We have found a beneficial process for the production of certain tetra- and pentafluoropropanes, which tetra- and pentafluoropropanes serve as preferred precursors for the manufacture of R-1234yf, R-1243zf and R-1234ze, especially R-1234yf and 1243zf.

Thus, according to a first aspect of the invention, there is provided a method of providing a blend of tetra- and pentafluoroalkanes comprising hydrogenating a pentafluoropropene.

Conveniently, the pentafluoropropene which is halogenated is 3,3,3,2,1-pentafluoropropene (R-1225ye), either Z or E isomers, or a mixture of both. R-1225ye (also known as HFC-1225ye) can exist as two stereoisomers, Z and E, which are known to have very similar boiling points, which can nevertheless be separated by standard distillation techniques. Our reference to R-1225ye encompasses both isomers, and also mixtures thereof. In some embodiments, preferably the isomers are present in a mass ratio of Z to E such that at last 50% of the R-1225ye exists as the Z isomer, even more preferably at least 80%.

Conveniently, the blend of tetra- and pentafluoropropanes which is prepared comprises 1,1,1,2,3 pentafluoropropane (R-245eb), preferably relatively high (e.g. greater than 8%, conveniently greater than 15% and in some instances conveniently greater than 20% by weight) levels of 1,1,1,2,3-pentafluoropropane.

In some instances, it is preferred that the resultant product stream comprises relatively high levels (e.g. greater than 30%, conveniently greater than 60%, and in some instances greater than 70% by weight) of tetrafluoropropanes.

It is particularly preferable that the resultant product stream be as rich as possible in 1,1,1,2,3-pentafluoropropane (R-245eb). R-245eb has been found to be a preferred precursor for the preparation of 3,3,3,2-tetrafluoropropene (R-1234yf). This is because R-1234yf can readily be prepared from R-245eb by a dehydrofluorination reaction; conversion to R-1234yf from R-245eb is more efficient and effective, and more readily happens than when it is prepared from other pentafluoropropanes. Whilst a number of routes exist to prepare R-1234yf from pentafluoropropanes, it has been found that the easiest dehydrofluorination reaction to perform to attain R-1234yf is that from R-245eb. For this reason, a process which produces relatively high levels of R-245eb is desirable.

That said, relatively desirable by-products of the hydrogenation reaction are the relatively high levels of various tetrafluoropropanes. These may also be advantageously converted into desirable products, for use for example in refrigerant blends, such as trifluoropropenes e.g. 1,1,1-trifluoropropene, (R-1243zf), again by use of a dehydrofluorination reaction.

The hydrogenation reaction carried out according to the invention may utilise any known hydrogenation conditions. However it is preferred that the hydrogenation is carried out using hydrogen and a catalyst, such as for example catalysts comprising transition metals such as palladium, platinum, ruthenium, rhenium, nickel, etc. The transition metal may be in any convenient form, for example unsupported, supported, finely divided or diluted. Suitable supports include those materials resistant to the chemical environment present when conducting the processes of the invention. Such materials include carbon, barium sulphate, calcium fluoride and alumina. Conveniently, the catalyst comprises palladium supported on carbon; the palladium levels in such a catalyst can conveniently be between 0.01% by weight and 10%, preferably 0.02% by weight to 5% by weight.

Conveniently the hydrogenation reaction is carried out at relatively low temperature, such as for example less than 150° C. Conveniently the temperature of the reaction can be 100° C. or less, conveniently 75° C. or less, conveniently 30° C. or less.

It has been found that a combination of relatively low temperature (e.g. 60° C. or less) and relatively high level of palladium loading on the catalyst (e.g. more than 1%, conveniently 3% by weight) leads to high levels of conversion of pentafluoropropene to a product mixture rich in tetrafluoropropanes. However, a combination of relatively high temperature (e.g. 75° C. or higher) and relatively low catalyst loading (e.g. less than 0.01% by weight, conveniently approximately 0.025% by weight) may lead to a reaction which is relatively specific (e.g. 94% by weight or more) in producing R-245eb.

In addition, it may also be preferred that the ratio of the volume of hydrogen to pentafluoropropene utilised in the reaction be relatively high, and conveniently greater than 1:1, for example in the range 1:1 to 4:1, 1:1 to 3:1, or 1:1 to 2:1.

The invention will now be described by way of example only.

EXPERIMENTAL

Example 1

A 3% Palladium on Sutcliffe-Speakman SS207C carbon was prepared by impregnation of the carbon support with aqueous palladium (II) chloride. In order to dissolve the palladium (II) chloride in water it was necessary to acidify the medium with hydrochloric acid until all the salt had dissolved. The catalyst was then dried. 2 g of 3% Palladium on Sutcliffe-Speakman SS207C carbon was loaded into an Inconel reactor tube. The reactor tube was purged with nitrogen (60 ml/min) and the catalyst further dried at 250° C. Hydrogen (16 ml/min) was then added to the nitrogen flow and the nitrogen flow stopped. This treatment was continued for 4 hours. A mixture of R-1225ye Z (>98%) and hydrogen was then passed over the catalyst at various flow rates and temperatures. Samples of the reactor off-gases were taken to determine their composition.

Example 2

Example 2 was performed exactly as Example 1 but the catalyst was replaced with a mixture of 0.5 g 0.5% Pd/C diluted in 9.5 g SS207C carbon.

Results

Example 1

The results are summarised in Table 1. High feed conversions were achieved without the need to supply any external heat to the reactor. Although R-245eb was detected in the reactor off-gas, the main product was a species identified as a tetrafluoropropane, $C_3H_4F_4$, R-254eb, $CF_3CHFCH_3$ using mass spectroscopy. This would be the product of the reductive dehydrofluorination of R-245eb:

$$CF_3CF = CHF \rightarrow CF_3CHFCH_2F \rightarrow CF_3CHFCH_3$$

It can be seen that the levels of R-245eb and R-254eb produced showed some dependence on the reactor conditions. Thus, the balance of products should be tunable by altering the reaction conditions, allowing primarily either R-245eb or R-254eb to be produced, or perhaps both.

Example 2

By using a diluted low Pd catalyst it was possible to demonstrate that the reaction could indeed be essentially stopped at the R-245eb stage thereby allowing R-245eb to be prepared selectively, see Table 2.

TABLE 1

| External Temperature (° C.) | R-1225ye flow (ml/min) | Hydrogen flow (ml/min) | R-1225ye Conversion (%) | GC Area % | | | | |
|---|---|---|---|---|---|---|---|---|
| | | | | R-1234yf | Z-1225ye | R-254eb | R-245eb | Others Incl. R-1243zf |
| 22 | 6.3 | 11.2 | 90.73 | 0.00 | 9.27 | 81.24 | 8.49 | 1.00 |
| 22 | 6.3 | 11.2 | 98.56 | 0.00 | 1.44 | 69.15 | 23.28 | 6.14 |
| 22 | 6.3 | 5 | 77.09 | 5.72 | 22.91 | 48.89 | 18.01 | 4.47 |
| 22 | 6 | 6 | 50.56 | 5.64 | 49.44 | 33.44 | 10.28 | 1.20 |
| 22 | 6 | 6 | 50.09 | 5.80 | 49.91 | 34.32 | 8.99 | 0.99 |
| 22 | 4 | 8 | 99.26 | 0.06 | 0.74 | 60.30 | 14.60 | 24.29 |
| 22 | 4 | 8 | 99.62 | 0.00 | 0.38 | 79.62 | 19.31 | 0.70 |
| 22 | 4 | 8 | 99.90 | 0.00 | 0.10 | 72.98 | 18.97 | 7.94 |
| 22 | 3 | 9 | 99.99 | 0.00 | 0.01 | 72.61 | 18.76 | 8.62 |
| 22 | 3 | 9 | 100.00 | 0.00 | 0.00 | 72.37 | 18.65 | 8.99 |
| 60 | 3 | 9 | 100.00 | 0.00 | 0.00 | 63.93 | 24.83 | 11.23 |
| 60 | 3 | 9 | 100.00 | 0.00 | 0.00 | 77.78 | 18.78 | 3.43 |

TABLE 2

| External Temperature (° C.) | R-1225ye flow (ml/min) | Hydrogen flow (ml/min) | R-1225ye Conversion (%) | GC Area % | | | | |
|---|---|---|---|---|---|---|---|---|
| | | | | R-1234yf | R-1225ye | R-254eb | R-245eb | Others Incl. R-1243zf |
| 100 | 3 | 9 | 14.2 | 0.0 | 85.8 | 0.1 | 12.0 | 2.1 |
| 100 | 4 | 8 | 13.4 | 0.0 | 86.6 | 0.6 | 11.3 | 1.4 |
| 100 | 6 | 6 | 9.3 | 0.0 | 90.7 | 0.2 | 7.0 | 2.1 |
| 75 | 6 | 6 | 7.7 | 0.0 | 92.3 | 0.0 | 4.7 | 3.0 |
| 75 | 4 | 8 | 7.3 | 0.0 | 92.7 | 0.0 | 6.0 | 1.3 |
| 75 | 3 | 9 | 9.2 | 0.0 | 90.8 | 0.0 | 7.0 | 2.2 |
| 125 | 3 | 9 | 18.5 | 0.4 | 81.5 | 0.1 | 14.6 | 3.4 |
| 125 | 4 | 8 | 18.5 | 0.1 | 81.5 | 0.3 | 16.0 | 2.2 |

The invention claimed is:

1. A method of providing a blend of at least two of R-254eb, R-245eb, R-1234yf, and R-1243zf, the blend also comprising unreacted R-1225ye, the method comprising hydrogenating R-1225ye, wherein the method is carried out at a temperature in the range of 75° C. to 125° C. in the presence of a Pd/C catalyst, wherein the catalyst metal loading is from 0.01% to 0.025% by weight of the bulk catalyst.

2. A method according to claim 1, wherein the resultant blend comprises at least 7% by weight 1,1,1,2,3 pentafluoropropane (R-245eb).

3. A method according to claim 1, wherein the hydrogenation reaction is carried out at 100° C. or less.

\* \* \* \* \*

UNITED STATES PATENT AND TRADEMARK OFFICE
CERTIFICATE OF CORRECTION

PATENT NO. : 8,471,078 B2
APPLICATION NO. : 12/735496
DATED : June 25, 2013
INVENTOR(S) : Low et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 148 days.

Signed and Sealed this
Eighth Day of September, 2015

Michelle K. Lee
*Director of the United States Patent and Trademark Office*